US009920013B2

(12) United States Patent
Beard et al.

(10) Patent No.: US 9,920,013 B2
(45) Date of Patent: Mar. 20, 2018

(54) 2,5-DIOXOIMIDAZOLIDIN-1-YL-3-UREA DERIVATIVES AS FORMYL PEPTIDE MODULATORS

(71) Applicant: Allergan, Inc., Irvine, CA (US)

(72) Inventors: Richard L. Beard, Newport Beach, CA (US); Vidyasagar Vuligonda, Irvine, CA (US); Thong Huy Vu, Garden Grove, CA (US); Michael E. Garst, Newport Beach, CA (US)

(73) Assignee: Allergan, Inc., Irvine, CA (US)

( * ) Notice: Subject to any disclaimer, the term of this patent is extended or adjusted under 35 U.S.C. 154(b) by 0 days.

(21) Appl. No.: 15/112,623

(22) PCT Filed: Jan. 27, 2015

(86) PCT No.: PCT/US2015/013021
§ 371 (c)(1),
(2) Date: Jul. 19, 2016

(87) PCT Pub. No.: WO2015/116566
PCT Pub. Date: Aug. 6, 2015

(65) Prior Publication Data
US 2016/0340318 A1 Nov. 24, 2016

Related U.S. Application Data

(60) Provisional application No. 61/932,943, filed on Jan. 29, 2014.

(51) Int. Cl.
*A61K 31/4166* (2006.01)
*C07D 233/80* (2006.01)

(52) U.S. Cl.
CPC .................. *C07D 233/80* (2013.01)

(58) Field of Classification Search
CPC .................. A61K 31/4166; C07D 233/80
See application file for complete search history.

(56) References Cited

U.S. PATENT DOCUMENTS

| 8,492,556 B2 * | 7/2013 | Beard ................. C07D 233/86 546/274.4 |
| 8,729,096 B2 | 5/2014 | Beard |
| 9,604,934 B2 | 3/2017 | Beard et al. |
| 2014/0256685 A1 | 9/2014 | Beard et al. |

FOREIGN PATENT DOCUMENTS

WO 2013-071203 5/2013

OTHER PUBLICATIONS

Chiang, Nan, et al., The Lipoxin Receptor ALX: Potent Ligand-Specific and Stereoselective Actions in Vivo, Pharmacological Reviews, 2006, 463-487, 58, No. 3.
Cross et al, Rules for the Nomenclature of Organic Chemistry, Pure & Appli. Chem, 1976, 11-30, vol. 45.
Dufton, Neil et al., Anti-Inflammatory Role of Murine Formyl-Peptide Receptor 2:Ligand-Specific Effects on Leukocyte Responses and Experimental Inflammation, Tthe Journal of Immunology, Jan. 2010, pp. 2611-2619, 184, The American Association of Immunologist, Inc., Bethesda, MD.
Gavins, Felicity N., et al., Leukocyte recruitment in the brain in sepsis: involvement of the annexin 1-FPR2/ALX anti-inflammatory system, FASEB J., Sep. 10, 2012, 4977-4989, 26.
Gronert, Karsten, Lipoxins in the eye and their role in wound healing, Prostaglandins, Leukotrienes and Essential Fatty Acids, 2005, pp. 221-229, 73, Elsevier Ltd.
Gronert, Karston, et al., A Role for the Mouse 12/15-Lipoxygenase Pathway in Promoting Epithelial Wound Healing and Host Defense, The Journal of Biological Chemistry, 2005, pp. 15267-15278, 280, No. 15.
Heinrich Stahl, Pharmaceutical Salts, Handbook of Pharmaceutical Salts, 2002, 329-345, International Union of Pure and Applied Chemistry, Verlag Helvetica Chemica Acta- Zurich.
Leedom, Alexander J., et al., Endogenous LXA4 Circuits Are Determinants of Pathological Angiogenesis in Response to Chronic Injury, The American Journal of Pathology, Jan. 2010, pp. 74-84, 176, No. 1, American Society for Investigative Pathology.
Maderna. Paola, et al., FPR2/ALX receptor expression and internalization are critical for lipoxin A4 and annexin-derived peptide-stimulated phagocytosis, FASEB J., Nov. 2010, 4240-4249, 24 (11).
Medeiros, Rodrigo, et al., Molecular Mechanisms of Topical Anti-Inflammatory Effects of Lipoxin A4 in Endotoxi-Induced Uveitis, Molecular Pharmacology, 2008, pp. 154-161, 74.
Patent Cooperation Treaty, Notification of Transmittal of the International Search Report & the Written Opinion of the International Searching Authority, or the Declaration, PCT/US2015/013021, Mar. 20, 2015, pp. 1-11.
Perretti, Mauro et al, Therapeutic Anti-Inflammatory Potential of Formyl-Peptide Receptor Agonists, Pharmacology & Research, 2010, 175-188, 127.

(Continued)

*Primary Examiner* — Golam M M Shameem
(74) *Attorney, Agent, or Firm* — Barbara C. Potts

(57) ABSTRACT

The present invention relates to 1-(2,5-dioxoimidazolidin-1-yl)-3-substituted urea compounds, processes for preparing them, pharmaceutical compositions containing them, their use as pharmaceuticals as modulators of the FPR2 receptor, and to methods of treating inflammatory diseases or conditions in a subject in need thereof by administering the compound(s) or pharmaceutical composition to the subject.

11 Claims, 1 Drawing Sheet

(56) References Cited

OTHER PUBLICATIONS

Reville, Keira, et al., Lipoxin A4 Redistributes Myosin IIA and Cdc42 in Macrophages: Implications for Phagocytosis of Apoptotic Leukocytes, The Journal of Immunology, 2006, pp. 1878-1888, 176.
Serhan, Charles N., Resolution Phase of Inflammation: Novel Endogenous Anti-Inflammatory and Proresolving Lipid Mediators and Pathways, The Annual Reviews of Immunology, 2007, pp. 101-37, 25, Annual reviews.
Takano, Tomoko, et al., Aspirin-triggered 15-Epi-Lipoxin-A4 (LXa4) and LXA4 Stable Analogues Are Potent Inbitiors of Acute Inflammation: Evidence for Anti-inflammatory Receptors, Journal of Experimental Medicine, May 5, 1997, 1693-1704, 185, No. 9, The Rockerfeller University Press.
Tsuruki, Takahiro, et al., Mechanism of the Protective Effect of Intraperitoneally Administered Agonists for Formyl Peptide Receptors against Chemotherapy-Induced Alpecia, Bioscience, Biotechnology & Biochemistry, 2007, pp. 1198-1202, 71, No. 5.
Yamasaki, Kenshi et al., Increased serine protease activity and cathelicidin promotes skin inflammation in rosacea, Nature Medicine, Aug. 2007, pp. 975-980, vol. 13, No. 8, Nature Publishing Group.

* cited by examiner

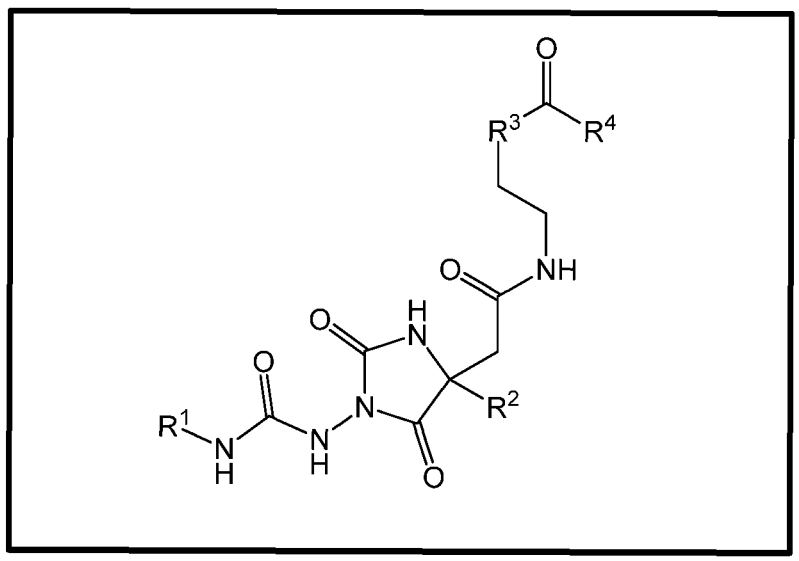

_US 9,920,013 B2_

2,5-DIOXOIMIDAZOLIDIN-1-YL-3-UREA DERIVATIVES AS FORMYL PEPTIDE MODULATORS

CROSS-REFERENCE TO RELATED APPLICATIONS

This application is a national stage application filed under 35 U.S.C. § 371 of International Patent Application Serial No. PCT/US2015/013021, filed on Jan. 27, 2015, which claims the benefit of U.S. Provisional Patent Application Ser. No. 61/932,943 filed on Jan. 29, 2014, the entire contents of each of which is incorporated herein by this specific reference.

FIELD OF THE INVENTION

The present invention relates to 1-(2,5-dioxoimidazolidin-1-yl)-3-substituted urea derivatives, processes for preparing them, pharmaceutical compositions containing them, and their use as pharmaceuticals as modulators of the N-formyl peptide 2 receptor (FPR2). The invention relates specifically to the use of these compounds and their pharmaceutical compositions to treat disorders associated with FPR2 modulation.

BACKGROUND OF THE INVENTION

The formyl peptide receptor (FPR) family belongs to the seven transmembrane domain G-protein-coupled receptor (GPCR) family. This family includes 3 members in humans, and one member of this family, FPR2 (also known as FPRL-1, ALXA4), is expressed predominantly on inflammatory cells such as monocytes and neutrophils, as well as on T cells, and has been shown to play a critical role in leukocyte trafficking during inflammation and human pathology (Chiang N, Serhan C N, Dahlen, S, Drazen J M, Hay D W P, Rovati E, Shimizu T, Yokomizo T, Brink, C. The lipoxin receptor ALX: Potent ligand-specific and stereoselective actions in vivo. Pharmacological Reviews 2006; 58: 463-519). FPR2 is an exceptionally promiscuous receptor that responds to a menagerie of structurally diverse exogenous and endogenous ligands, including serum amyloid A (SAA), chemokine variant sCKβ8-1, the neuroprotective peptide humanin, anti-inflammatory eicosanoid lipoxin A4 (LXA4) and glucocorticoid-modulated protein annexin A1 (Chiang N, Serhan C N, Dahlen, S, Drazen J M, Hay D W P, Rovati E, Shimizu T, Yokomizo T, Brink, C. The lipoxin receptor ALX: Potent ligand-specific and stereoselective actions in vivo. Pharmacological Reviews 2006; 58: 463-519). FPR2 has been shown to transduce anti-inflammatory effects of arachidonic acid derived lipoxin A4 (LXA4) in many systems, and has been shown to play a key role in the resolution of inflammation (Dufton N, Perretti M. Therapeutic anti-inflammatory potential of formyl peptide receptor agonists. Pharmacology & Therapeutics 2010; 127: 175-188). FPR2 knockout mice show exaggerated inflammation in disease conditions as expected by the biological role of the receptor (Dufton N, Hannon R, Brancaleone V, Dalli J, Patel H B, Gray M, D'Aquisto F, Buckingham J C, Perretti M, Flower R J. Anti-inflammatory role of the murine formyl-peptide receptor 2: Ligand-specific effects on leukocyte responses and experimental inflammation. Journal of Immunology 2010; 184: 2611-2619. Gavins F N E, Hughes E L, Buss N A P S, Holloway P M, Getting S J, Buckingham J C. Leukocyte recruitment in the brain in sepsis: involvement of the annexin1 FPR2/ALX anti-inflammatory system. FASEB 2012; 26: 1-13).

Activation of FPR2 by lipoxin A4 or its analogs and by Annexin I protein has been shown to result in anti-inflammatory activity by promoting active resolution of inflammation which involves inhibition of polymorphonuclear neutrophils (PMNs) and eosinophils migration and also stimulating monocyte migration enabling clearance of apoptotic cells from the site of inflammation in a nonphlogistic manner (Gavins F N E, Hughes E L, Buss N A P S, Holloway P M, Getting S J, Buckingham J C. Leukocyte recruitment in the brain in sepsis: involvement of the annexin1 FPR2/ALX anti-inflammatory system. FASEB 2012; 26: 1-13, Maderna P, Cottell D C, Toivonen T, Dufton N, Dalli J, Perretti M, Godson C. FPR2/ALX receptor expression and internalization are critical for lipoxin A4 and annexin-derived peptide-stimulated phagocytosis. FASEB 2010; 24: 4240-4249). In addition, FPR2 has been shown to inhibit natural killer (NK) cytotoxicity and promote activation of T cells which further contributes to down regulation of tissue damaging inflammatory signals.

FPR2 interaction with LXA4 and Annexin has been shown to be beneficial in experimental models of dermal inflammation, angiogenesis, epithelial migration, edema, alopecia, ischemia reperfusion and ocular inflammation, such as endotoxin-induced uveitis and corneal wound healing (Reville K, Cream J K, Vivers S, Dransfield I, Godson C. Lipoxin A4 redistributes Mysoin IIA and Cdc42 in macrophages: Implications for phagocytosis of apoptotic leukocytes. Journal of Immunology 2006; 176: 1878-1888; Serhan C. Resolution phase of inflammation: Novel endogenous anti-inflammatory and proresolving lipid mediators and pathways. Annual reviews of Immunology 2007; 25: 101-137; Medeiros R, Rodrigues G B, Figueiredo C P, Rodrigues E B, Grumman A Jr, Menezes-de-Lima O Jr, Passos G F, Calixto J B. Molecular mechanisms of topical anti-inflammatory effects of lipoxin A(4) in endotoxin-induced uveitis. _Molecular Pharmacology_ 2008; 74: 154-161; Gronert K, Maheshwari N, Khan N, Hassan I R, Dunn M, Schwartzmann M L. A role for the mouse 12/15-lipoxygenase pathways in promoting epithelial wound healing and host defense. Journal of Biological Chemistry 2005; 280: 15267-15278; Gronert K. Lipoxins in the eye and their role in wound healing. _Prostaglandins, Leukotrienes and Essential fatty Acids._ 2005; 73: 221-229; Takano T, Fiore S, Maddox J F, Brady H R, Petasis N A, Serhan C N. Aspirin-triggered 15-epi-lipoxin A4 and LXA4 stable analogues are potent inhibitors of acute inflammation: evidence for anti-inflammatory receptors. Journal of Experimental Medicine 1997; 185: 1693-1704; Leoni G, Alam A, Neumann P A, Lambeth J D, Cheng G, McCoy J, Hilgarth R S, Kundu K, Murthy N, Kusters D, Reutelingsperger C, Perretti M, Parkos C A, Neish A S, Nusrat A. Annexin A1, formyl peptide receptor, and NOX1 orchestrate epithelial repair. Journal of Clinical Investigation. 2013; 123:443-54; Leedom A, Sullivan A B, Dong B, Lau D, Gronert K. Endogenous LXA4 circuits are determinants of pathological angiogenesis in response to chronic injury. American Journal of Pathology 2010; 176: 74-84; Tsuruki T, Takahata K, Yoshikawa M. Mechanism of the protective effect of intraperitoneally administered agonists for formyl peptide receptors against chemotherapy-induced alopecia. Biosci Biotechnology Biochemistry. Biochemistry, 2007; 71:1198-202).

Pharmaceutical utility of lipoxin A4 and its analogs are hampered by inherent physicochemical properties of the natural poly-olefinic natural product. Therefore, small molecule anti-inflammatory agonists of FPR2 would have a wide variety of therapeutic benefit in inflammatory disorders, including inflammatory disorders in the eye. Targeting FPR2 selectively would also have benefits of reduced side effects as compared to more broad acting anti-inflammatories such as steroids or NSAIDs which have significant side effects of elevated IOP and delays in wound healing in the eye. FPR2 is also expressed in ocular tissues in the cornea and also the posterior of eye, in addition to the inflammatory cells that migrate into the ocular tissues.

Targeting FPR2 selectively would also have benefits in skin wound healing given its potent anti-inflammatory and pro-epithelial repair role. In addition, some skin diseases have been shown to have an abnormal expression of LL37, a pro-inflammatory cathelicidin which has been shown to be a natural ligand of FPR2. In the chronic inflammatory disease rosacea, LL37 is highly expressed and is believed to play a key role in the pathogenesis (Yamasaki K, Di Nardo A, Bardan A, Murakami M, Ohtake T, Coda A, Dorschner R A, Bonnart C, Descargues P, Hovnanian A, Morhenn V B, Gallo R L. Increased serine protease activity and cathelicidin promotes skin inflammation in rosacea. Nature Medicine. 2007; 13:975-80).

FPR2 thus represents an important novel pro-resolutionary molecular target for the development of new therapeutic agents in diseases or conditions with excessive inflammatory responses.

U.S. Pat. No. 8,492,556 teaches 2,5-dioxoimidazolidin-1-yl-3-phenylurea derivatives as formyl peptide modulators like-1 receptor modulators.

SUMMARY OF THE INVENTION

A group of novel compounds, which are potent and selective FPR2 modulators, has been discovered. As such, the compounds described herein are useful in treating a wide variety of disorders associated with modulation of FPR2 receptor. The term "modulator" as used herein, includes but is not limited to: receptor agonist, antagonist, inverse agonist, inverse antagonist, partial agonist, and partial antagonist.

This invention describes compounds of Formula I, which have FPR2 receptor biological activity. The compounds in accordance with the present invention are thus of use in medicine, for example, in the treatment of humans with diseases and conditions that are alleviated by FPR2 modulation.

In one aspect, the invention provides a compound having Formula I:

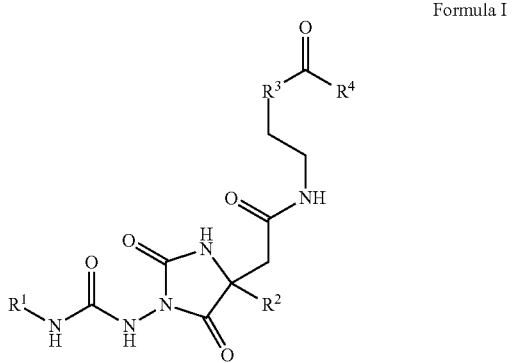

Formula I wherein:
$R^1$ is substituted or unsubstituted $C_{1-8}$alkyl, substituted or unsubstituted $C_{3-8}$cycloalkyl, substituted or unsubstituted $C_6$-$C_{10}$aryl, or substituted or unsubstituted heterocycle;
$R^2$ is hydrogen, or substituted or unsubstituted $C_{1-8}$alkyl;
$R^3$ is O or $NR^5$;
$R^4$ is $C_{1-4}$alkyl; and
$R^5$ is hydrogen, substituted or unsubstituted $C_{1-8}$alkyl, —C(O)$C_{1-8}$alkyl, substituted or unsubstituted $C_6$-$C_{10}$aryl, or substituted or unsubstituted heterocycle;
or an enantiomer, diastereomer or tautomer thereof;
or a zwitterion or pharmaceutically acceptable salt of any one of the foregoing.

In another embodiment, the invention relates to a compound according to Formula I, wherein:
$R^1$ is substituted $C_6$ aryl;
$R^2$ is hydrogen, methyl, ethyl, n-propyl or isopropyl;
$R^3$ is O or $NR^5$;
$R^4$ is methyl; and
$R^5$ is hydrogen.

In another embodiment, the invention relates to a compound according to Formula I, wherein:
$R^1$ is substituted phenyl;
$R^2$ is hydrogen, methyl, ethyl, n-propyl or isopropyl;
$R^3$ is O; and
$R^4$ is methyl.

In another embodiment, the invention relates to a compound according to Formula I, wherein:
$R^1$ is 4-bromo-phenyl;
$R^2$ is hydrogen, methyl, ethyl, n-propyl or isopropyl;
$R^3$ is O; and
$R^4$ is methyl.

In another embodiment, the invention relates to a compound according to Formula I, wherein:
$R^1$ is substituted phenyl;
$R^2$ is hydrogen, methyl, ethyl, n-propyl or isopropyl;
$R^3$ is $NR^5$;
$R^4$ is methyl; and
$R^5$ is hydrogen.

In another embodiment, the invention relates to a compound according to Formula I, wherein:
$R^1$ is 4-bromo-phenyl;
$R^2$ is hydrogen, methyl, ethyl, n-propyl or isopropyl;
$R^3$ is $NR^5$;
$R^4$ is methyl; and
$R^5$ is hydrogen.

In another embodiment, the invention relates to a compound according to Formula I, wherein:
$R^1$ is 4-bromo-2-fluorophenyl;
$R^2$ is hydrogen, methyl, ethyl, n-propyl or isopropyl;
$R^3$ is $NR^5$;
$R^4$ is methyl; and $R^5$ is hydrogen.

In another embodiment, the invention relates to a compound according to Formula I, wherein:
$R^1$ is 4-bromo-2-fluorophenyl;
$R^2$ is hydrogen, methyl, ethyl, n-propyl or isopropyl;
$R^3$ is O; and
$R^4$ is methyl.

The term "alkyl", as used herein, refers to saturated, monovalent or divalent hydrocarbon moieties having linear or branched moieties or combinations thereof and containing 1 to 8 carbon atoms (i.e., $C_{1-8}$alkyl); one methylene (—$CH_2$—) group of the alkyl group can be replaced by oxygen, sulfur, sulfoxide, —N($R^x$)— (wherein $R^x$ is H, OH, or optionally substituted $C_{1-8}$ alkyl), carbonyl, carboxyl, sulfonyl, sulfate, sulfonate, amide, sulfonamide, by a divalent $C_{3-8}$ cycloalkyl, by a divalent heterocycle, or by a divalent aryl group. Alkyl groups can have one or more chiral centers. Alkyl groups can be independently substituted with one or more halogen atoms, hydroxyl groups, —OC$_{1-8}$ alkyl groups, cycloalkyl groups, amino groups, heterocyclic groups, aryl groups, carboxylic acid groups, phosphonic acid groups, sulphonic acid groups, phosphoric acid groups, nitro groups, amide groups, sulfonamide groups, ester groups, and/or ketone groups. In some embodiments, the alkyl is a C$_{1-4}$alkyl, which refers to saturated, monovalent or divalent hydrocarbon moieties having linear or branched moieties or combinations thereof and containing 1 to 4 carbon atoms, including methyl, ethyl, propyl, isopropyl, butyl, tert-butyl, isobutyl and sec-butyl.

The term "cycloalkyl", as used herein, refers to a monovalent or divalent group of 3 to 8 carbon atoms derived from a saturated cyclic hydrocarbon. Cycloalkyl groups can be monocyclic or polycyclic. Cycloalkyl can be independently substituted with one or more halogen atoms, sulfonyl C$_{1-8}$ alkyl groups, sulfoxide C$_{1-8}$ alkyl groups, sulfonamide groups, nitro groups, —OC$_{1-8}$ alkyl groups, —SC$_{1-8}$ alkyl groups, —C$_{1-8}$ alkyl groups, ketone groups, alkylamino groups, amino groups, aryl groups, C$_{3-8}$ cycloalkyl groups and/or hydroxyl groups.

The term "cycloalkenyl", as used herein, refers to a monovalent or divalent group of 3 to 8 carbon atoms derived from a saturated cycloalkyl having at least one double bond. Cycloalkenyl groups can be monocyclic or polycyclic. Cycloalkenyl groups can be independently substituted with one or more halogen atoms, sulfonyl groups, sulfoxide groups, nitro groups, —OC$_{1-6}$ alkyl groups, —SC$_{1-6}$ alkyl groups, —C$_{1-6}$ alkyl groups, ketone groups, alkylamino groups, amino groups, aryl groups, C$_{3-8}$ cycloalkyl groups and/or hydroxyl groups.

The term "halogen", as used herein, refers to an atom of fluorine, chlorine, bromine, iodine.

The term "heterocycle" as used herein, refers to a 3 to 10 membered ring, which can be aromatic or non-aromatic, saturated or unsaturated, containing at least one heteroatom selected from oxygen, nitrogen, sulfur, or combinations of at least two thereof, interrupting the carbocyclic ring structure. The heterocyclic ring can be interrupted by a C=O; the S and N heteroatoms can be oxidized. Heterocycles can be monocyclic or polycyclic. Heterocyclic ring moieties can be substituted with one or more halogen atoms, sulfonyl groups, sulfoxide groups, nitro groups, —OC$_{1-8}$ alkyl groups, —SC$_{1-8}$ alkyl groups, —C$_{1-8}$ alkyl groups, ketone groups, alkylamino groups, amino groups, aryl groups, C$_{3-8}$ cycloalkyl groups and/or hydroxyl groups.

The term "aryl" as used herein, refers to an organic moiety derived from an aromatic hydrocarbon consisting of a ring containing 6 to 10 carbon atoms, by removal of one hydrogen atom. Aryl can be substituted with one or more halogen atoms, sulfonyl C$_{1-8}$ alkyl groups, sulfoxide C$_{1-8}$ alkyl groups, sulfonamide groups, carboxylic acid groups, C$_{1-8}$ alkyl carboxylates (ester) groups, amide groups, nitro groups, —OC$_{1-6}$ alkyl groups, —SC$_{1-8}$ alkyl groups, —C$_{1-8}$ alkyl groups, ketone groups, alkylamino groups, amino groups, C$_{3-8}$ cycloalkyl groups and/or hydroxyl groups. Aryls can be monocyclic or polycyclic.

The term "hydroxyl" as used herein, represents a group of formula "—OH".

The term "carbonyl" as used herein, represents a group of formula "—C(O)—".

The term "ketone" as used herein, represents an organic compound having a carbonyl group linked to a carbon atom such as —C(O)R$^x$ wherein R$^x$ can be alkyl, aryl, cycloalkyl, cycloalkenyl or heterocycle, as defined above.

The term "ester" as used herein, represents an organic compound having a carbonyl group linked to a carbon atom such as —C(O)OR$^x$ wherein R$^x$ can be alkyl, aryl, cycloalkyl, cycloalkenyl or heterocycle, as defined above.

The term "amine" as used herein, represents a group of formula "—NR$^x$R$^y$", wherein R$^x$ and R$^y$ can be the same or independently H, alkyl, aryl, cycloalkyl, cycloalkenyl or heterocycle, as defined above.

The term "carboxyl" as used herein, represents a group of formula "—C(O)O—".

The term "sulfonyl" as used herein, represents a group of formula "—SO$_2$—".

The term "sulfate" as used herein, represents a group of formula "—OS(O)$_2$O—".

The term "sulfonate" as used herein, represents a group of the formula "—S(O)$_2$O—".

The term "carboxylic acid" as used herein, represents a group of formula "—C(O)OH".

The term "nitro" as used herein, represents a group of formula "—NO$_2$".

The term "amide" as used herein, represents a group of formula "—C(O)NR$^x$R$^y$," wherein R$^x$ and R$^y$ can be the same or independently H, alkyl, aryl, cycloalkyl, cycloalkenyl or heterocycle, as defined above.

The term "sulfonamide" as used herein, represents a group of formula "—S(O)$_2$NR$^x$R$^y$" wherein R$^x$ and R$^y$ can be the same or independently H, alkyl, aryl, cycloalkyl, cycloalkenyl or heterocycle, as defined above.

The term "sulfoxide" as used herein, represents a group of formula "—S(O)—".

The term "phosphonic acid" as used herein, represents a group of formula "—P(O)(OH)$_2$".

The term "phosphoric acid" as used herein, represents a group of formula "—OP(O)(OH)$_2$".

The term "sulphonic acid" as used herein, represents a group of formula "—S(O)$_2$OH".

The formula "H", as used herein, represents a hydrogen atom.

The formula "O", as used herein, represents an oxygen atom.

The formula "N", as used herein, represents a nitrogen atom.

The formula "S", as used herein, represents a sulfur atom.

Some compounds of the invention are:
N-[2-(acetylamino)ethyl]-2-[1-{[(4-bromophenyl)carbamoyl]amino}-2,5-dioxo-4-(propan-2-yl)imidazolidin-4-yl]acetamide;
2-({1-{[(4-bromo-2-fluorophenyl)carbamoyl]amino}-2,5-dioxo-4-(propan-2-yl)imidazolidin-4-yl]acetyl}amino)ethyl acetate; and
2-({1-{[(4-bromophenyl)carbamoyl]amino}-2,5-dioxo-4-(propan-2-yl)imidazolidin-4-yl]acetyl}amino)ethyl acetate.

Some compounds of Formula I and some of their intermediates have at least one asymmetric center in their structure. This asymmetric center may be present in an R or S configuration, said R and S notation is used in correspondence with the rules described in Pure Appl. Chem. (1976), 45, 11-13.

The term "pharmaceutically acceptable salts" refers to salts or complexes that retain the desired biological activity of the above identified compounds and exhibit minimal or no undesired toxicological effects. The "pharmaceutically acceptable salts" according to the invention include therapeutically active, non-toxic base or acid salt forms, which the compounds of Formula I are able to form.

The acid addition salt form of a compound of Formula I that occurs in its free form as a base can be obtained by treating the free base with an appropriate acid such as an inorganic acid, for example, hydrochloric acid, hydrobromic acid, sulfuric acid, phosphoric acid, nitric acid and the like; or an organic acid such as for example, acetic acid, hydroxyacetic acid, propanoic acid, lactic acid, pyruvic acid, malonic acid, fumaric acid, maleic acid, oxalic acid, tartaric acid, succinic acid, malic acid, ascorbic acid, benzoic acid, tannic acid, pamoic acid, citric acid, methylsulfonic acid, ethanesulfonic acid, benzenesulfonic acid, formic and the like (Handbook of Pharmaceutical Salts, P. Heinrich Stahl & Camille G. Wermuth (Eds), Verlag Helvetica Chimica Acta-Zürich, 2002, 329-345).

The base addition salt form of a compound of Formula I that occurs in its acid form can be obtained by treating the acid with an appropriate base such as an inorganic base, for example, sodium hydroxide, magnesium hydroxide, potassium hydroxide, calcium hydroxide, ammonia and the like; or an organic base such as for example, L-Arginine, ethanolamine, betaine, benzathine, morpholine and the like. (Handbook of Pharmaceutical Salts, P. Heinrich Stahl & Camille G. Wermuth (Eds), Verlag Helvetica Chimica Acta-Zürich, 2002, 329-345).

The compounds of the invention are indicated for use in treating or preventing conditions in which there is likely to be a component involving the N-formyl peptide receptor 2.

In a further embodiment of the invention, there are provided methods for treating disorders associated with modulation of the N-formyl peptide 2 receptor. Such methods can be performed, for example, by administering to a subject in need thereof a pharmaceutical composition containing a therapeutically effective amount of at least one compound of the invention.

Therapeutic utilities of the N-formyl peptide 2 receptor modulators are ocular inflammatory diseases and conditions including, but not limited to, wet and dry age-related macular degeneration (ARMD), uveitis, dry eye, keratitis, allergic eye disease and conditions affecting the posterior part of the eye, such as maculopathies and retinal degeneration including non-exudative age related macular degeneration, exudative age related macular degeneration, choroidal neovascularization, diabetic retinopathy (proliferative), retinopathy of prematurity (ROP), acute macular neuroretinopathy, central serous chorioretinopathy, cystoid macular edema, and diabetic macular edema; infectious keratitis, herpetic keratitis, corneal angiogenesis, lymphangiogenesis, retinitis, choroiditis such as acute multifocal placoid pigment epitheliopathy, Behcet's disease, birdshot retinochoroidopathy, infectious (syphilis, lyme, tuberculosis, toxoplasmosis), intermediate uveitis (pars planitis), multifocal choroiditis, multiple evanescent white dot syndrome (mewds), ocular sarcoidosis, posterior scleritis, serpiginous choroiditis, subretinal fibrosis and uveitis syndrome, Vogt-Koyanagi- and Harada syndrome; vascular diseases/exudative diseases such as retinal arterial occlusive disease, central retinal vein occlusion, cystoids macular edema, disseminated intravascular coagulopathy, branch retinal vein occlusion, hypertensive fundus changes, ocular ischemic syndrome, retinal arterial microaneurysms, Coat's disease, parafoveal telangiectasis, hemiretinal vein occlusion, papillophlebitis, central retinal artery occlusion, branch retinal artery occlusion, carotid artery disease (CAD), frosted branch angiitis, sickle cell retinopathy and other hemoglobinopathies, angioid streaks, familial exudative vitreoretinopathy, and Eales disease; traumatic/surgical conditions such as sympathetic ophthalmia, uveitic retinal disease, retinal detachment, trauma, post surgical corneal wound healing, post-cataract surgical inflammation, conditions caused by laser, conditions caused by photodynamic therapy, photocoagulation, hypoperfusion during surgery, radiation retinopathy, and bone marrow transplant retinopathy; proliferative disorders such as proliferative vitreal retinopathy and epiretinal membranes, and proliferative diabetic retinopathy; infectious disorders such as ocular histoplasmosis, ocular toxocariasis, presumed ocular histoplasmosis syndrome (POHS), endophthalmitis, toxoplasmosis, retinal diseases associated with HIV infection, choroidal disease associate with HIV infection, uveitic disease associate with HIV infection, viral retinitis, acute retinal necrosis, progressive outer retinal necrosis, fungal retinal diseases, ocular syphilis, ocular tuberculosis, diffuse unilateral subacute neuroretinitis, and myiasis; genetic disorders such as retinitis pigmentosa, systemic disorders with associated retinal dystrophies, congenital stationary night blindness, cone dystrophies, Stargardt's disease and fundus flavimaculatus, Best's disease, pattern dystrophy of the retinal pigmented epithelium, X-linked retinoschisis, Sorsby's fundus dystrophy, benign concentric maculopathy, Bietti's crystalline dystrophy, and pseudoxanthoma elasticum; retinal tears/holes such as retinal detachment, macular hole, and giant retinal tear; tumors such as retinal disease associated with tumors, congenital hypertrophy of the retinal pigmented epithelium, posterior uveal melanoma, choroidal hemangioma, choroidal osteoma, choroidal metastasis, combined hamartoma of the retina and retinal pigmented epithelium, retinoblastoma, vasoproliferative tumors of the ocular fundus, retinal astrocytoma, and intraocular lymphoid tumors; and miscellaneous other diseases affecting the posterior part of the eye such as punctate inner choroidopathy, acute posterior multifocal placoid pigment epitheliopathy, myopic retinal degeneration, and acute retinal pigment epitheliitis, systemic inflammatory diseases such as stroke, coronary artery disease, obstructive airway diseases, HIV-mediated retroviral infections, cardiovascular disorders including coronary artery disease, neuroinflammation, neurological disorders, pain and immunological disorders, rheumatoid arthritis and related inflammatory disorders, asthma, allergic disorders, inflammation, systemic lupus erythematosus, CNS disorders such as Alzheimer's disease, arthritis, sepsis, inflammatory bowel disease, cachexia, angina pectoris, post-surgical corneal inflammation, blepharitis, meibomian gland dysfunction; glaucoma, branch vein occlusion, Best's vitelliform macular degeneration, retinitis pigmentosa, proliferative vitreoretinopathy (PVR), and any other degenerative disease of either the photoreceptors or the RPE (Perretti, Mauro et al. Pharmacology & Therapeutics 127 (2010) 175-188). Therapeutic utilities of the N-formyl peptide 2 receptor modulators also include the treatment of dermal inflammation and dermal diseases including but not limited to dermal wound healing, hypertrophic scars, keloids, burns, rosacea, atopic dermatitis, acne, psoriasis, seborrheic dermatitis, actinic keratoses, basal cell carcinoma, squamous cell carcinoma, melanoma, viral warts, photoaging, photodamage, melasma, post-inflammatory hyperpigmentation, disorders of pigmentation, alopecia, scarring and non-scarring forms.

The compounds described herein are useful for the treatment of mammals, including humans, with a range of conditions and diseases that are alleviated by FPR2 modulation: including, but not limited to the treatment of ocular inflammatory diseases: wet and dry age-related macular degeneration (ARMD), uveitis, dry eye, keratitis, allergic eye disease and conditions affecting the posterior part of the eye, such as maculopathies and retinal degeneration including non-exudative age related macular degeneration, exudative age related macular degeneration, choroidal neovascularization, diabetic retinopathy (proliferative), retinopathy of prematurity (ROP), acute macular neuroretinopathy, central serous chorioretinopathy, cystoid macular edema, and diabetic macular edema; infectious keratitis, herpetic keratitis, corneal angiogenesis, lymphangiogenesis, retinitis, choroiditis such as acute multifocal placoid pigment epitheliopathy, Behcet's disease, birdshot retinochoroidopathy, infectious (syphilis, lyme, tuberculosis, toxoplasmosis), intermediate uveitis (pars planitis), multifocal choroiditis, multiple evanescent white dot syndrome (mewds), ocular sarcoidosis, posterior scleritis, serpiginous choroiditis, subretinal fibrosis and uveitis syndrome, Vogt-Koyanagi- and Harada syndrome; vascular diseases/exudative diseases such as retinal arterial occlusive disease, central retinal vein occlusion, cystoids macular edema, disseminated intravascular coagulopathy, branch retinal vein occlusion, hypertensive fundus changes, ocular ischemic syndrome, retinal arterial microaneurysms, Coat's disease, parafoveal telangiectasis, hemi-retinal vein occlusion, papillophlebitis, central retinal artery occlusion, branch retinal artery occlusion, carotid artery disease (CAD), frosted branch angiitis, sickle cell retinopathy and other hemoglobinopathies, angioid streaks, familial exudative vitreoretinopathy, and Eales disease; traumatic/surgical conditions such as sympathetic ophthalmia, uveitic retinal disease, retinal detachment, trauma, post surgical corneal wound healing, post-cataract surgical inflammation, conditions caused by laser, conditions caused by photodynamic therapy, photocoagulation, hypoperfusion during surgery, radiation retinopathy, and bone marrow transplant retinopathy; proliferative disorders such as proliferative vitreal retinopathy and epiretinal membranes, and proliferative diabetic retinopathy; infectious disorders such as ocular histoplasmosis, ocular toxocariasis, presumed ocular histoplasmosis syndrome (POHS), endophthalmitis, toxoplasmosis, retinal diseases associated with HIV infection, choroidal disease associate with HIV infection, uveitic disease associate with HIV infection, viral retinitis, acute retinal necrosis, progressive outer retinal necrosis, fungal retinal diseases, ocular syphilis, ocular tuberculosis, diffuse unilateral subacute neuroretinitis, and myiasis; genetic disorders such as retinitis pigmentosa, systemic disorders with associated retinal dystrophies, congenital stationary night blindness, cone dystrophies, Stargardt's disease and fundus flavimaculatus, Best's disease, pattern dystrophy of the retinal pigmented epithelium, X-linked retinoschisis, Sorsby's fundus dystrophy, benign concentric maculopathy, Bietti's crystalline dystrophy, and pseudoxanthoma elasticum; retinal tears/holes such as retinal detachment, macular hole, and giant retinal tear; tumors such as retinal disease associated with tumors, congenital hypertrophy of the retinal pigmented epithelium, posterior uveal melanoma, choroidal hemangioma, choroidal osteoma, choroidal metastasis, combined hamartoma of the retina and retinal pigmented epithelium, retinoblastoma, vasoproliferative tumors of the ocular fundus, retinal astrocytoma, and intraocular lymphoid tumors; and miscellaneous other diseases affecting the posterior part of the eye such as punctate inner choroidopathy, acute posterior multifocal placoid pigment epitheliopathy, myopic retinal degeneration, and acute retinal pigment epitheliitis, systemic inflammatory diseases such as stroke, coronary artery disease, obstructive airway diseases, HIV-mediated retroviral infections, cardiovascular disorders including coronary artery disease, neuroinflammation, neurological disorders, pain and immunological disorders, rheumatoid arthritis and related inflammatory disorders, asthma, allergic disorders, inflammation, systemic lupus erythematosus, CNS disorders such as Alzheimer's disease, arthritis, sepsis, inflammatory bowel disease, cachexia, angina pectoris, post-surgical corneal inflammation, blepharitis, meibomian gland dysfunction; glaucoma, branch vein occlusion, Best's vitelliform macular degeneration, retinitis pigmentosa, proliferative vitreoretinopathy (PVR), and any other degenerative disease of either the photoreceptors or the RPE (Perretti, Mauro et al. Pharmacology & Therapeutics 127 (2010) 175-188). These compounds are useful for the treatment of dermal inflammation and dermal diseases including but not limited to dermal wound healing, hypertrophic scars, keloids, burns, rosacea, atopic dermatitis, acne, psoriasis, seborrheic dermatitis, actinic keratoses, basal cell carcinoma, squamous cell carcinoma, melanoma, viral warts, photoaging, photodamage, melasma, post-inflammatory hyperpigmentation, disorders of pigmentation, alopecia, scarring and non-scarring forms.

In still another embodiment of the invention, there are provided methods for treating disorders associated with modulation of the FPR2 receptor. Such methods can be performed, for example, by administering to a subject in need thereof a therapeutically effective amount of at least one compound of the invention, or any combination thereof, or pharmaceutically acceptable salts, individual enantiomers, and/or diastereomers thereof.

The present invention concerns the use of a compound of Formula I or a pharmaceutically acceptable salt thereof, for the manufacture of a medicament for the treatment of ocular inflammatory diseases including, but not limited to, wet and dry age-related macular degeneration (ARMD), uveitis, dry eye, keratitis, allergic eye disease and conditions affecting the posterior part of the eye, such as maculopathies and retinal degeneration including non-exudative age related macular degeneration, exudative age related macular degeneration, choroidal neovascularization, diabetic retinopathy (proliferative), retinopathy of prematurity (ROP), acute macular neuroretinopathy, central serous chorioretinopathy, cystoid macular edema, and diabetic macular edema; infectious keratitis, herpetic keratitis, corneal angiogenesis, lymphangiogenesis, uveitis, retinitis, and choroiditis such as acute multifocal placoid pigment epitheliopathy, Behcet's disease, birdshot retinochoroidopathy, infectious (syphilis, lyme, tuberculosis, toxoplasmosis) intermediate uveitis (pars planitis), multifocal choroiditis, multiple evanescent white dot syndrome (mewds), ocular sarcoidosis, posterior scleritis, serpiginous choroiditis, subretinal fibrosis and uveitis syndrome, Vogt-Koyanagi- and Harada syndrome; vascular diseases/exudative diseases such as retinal arterial occlusive disease, central retinal vein occlusion, cystoids macular edema, disseminated intravascular coagulopathy, branch retinal vein occlusion, hypertensive fundus changes, ocular ischemic syndrome, retinal arterial microaneurysms, Coat's disease, parafoveal telangiectasis, hemi-retinal vein occlusion, papillophlebitis, central retinal artery occlusion, branch retinal artery occlusion, carotid artery disease (CAD), frosted branch angiitis, sickle cell retinopathy and other hemoglobinopathies, angioid streaks, familial exudative vitreoretinopathy, and Eales disease; traumatic/surgical conditions such as sympathetic ophthalmia, uveitic retinal disease, retinal detachment, trauma, post surgical corneal wound healing or inflammation, post-cataract surgical inflammation, wet and dry age-related macular degeneration (ARMD), conditions caused by laser, conditions caused by photodynamic therapy, photocoagulation, hypoperfusion during surgery, radiation retinopathy, and bone marrow transplant retinopathy; proliferative disorders such as proliferative vitreal retinopathy and epiretinal membranes, and proliferative diabetic retinopathy; infectious disorders such as ocular histoplasmosis, ocular toxocariasis, presumed ocular histoplasmosis syndrome (POHS), endophthalmitis, toxoplasmosis, retinal diseases associated with HIV infection, choroidal disease associate with HIV infection, uveitic disease associate with HIV infection, viral retinitis, acute retinal necrosis, progressive outer retinal necrosis, fungal retinal diseases, ocular syphilis, ocular tuberculosis, diffuse unilateral subacute neuroretinitis, and myiasis; genetic disorders such as retinitis pigmentosa, systemic disorders with associated retinal dystrophies, congenital stationary night blindness, cone dystrophies, Stargardt's disease and fundus flavimaculatus, Best's disease, pattern dystrophy of the retinal pigmented epithelium, X-linked retinoschisis, Sorsby's fundus dystrophy, benign concentric maculopathy, Bietti's crystalline dystrophy, and pseudoxanthoma elasticum; retinal tears/holes such as retinal detachment, macular hole, and giant retinal tear; tumors such as retinal disease associated with tumors, congenital hypertrophy of the retinal pigmented epithelium, posterior uveal melanoma, choroidal hemangioma, choroidal osteoma, choroidal metastasis, combined hamartoma of the retina and retinal pigmented epithelium, retinoblastoma, vasoproliferative tumors of the ocular fundus, retinal astrocytoma, and intraocular lymphoid tumors; and miscellaneous other diseases affecting the posterior part of the eye such as punctate inner choroidopathy, acute posterior multifocal placoid pigment epitheliopathy, myopic retinal degeneration, and acute retinal pigment epitheliitis, systemic inflammatory diseases such as stroke, coronary artery disease, obstructive airway diseases, HIV-mediated retroviral infections, cardiovascular disorders including coronary artery disease, neuroinflammation, neurological disorders, pain and immunological disorders, rheumatoid arthritis and related inflammatory disorders, asthma, allergic disorders, inflammation, systemic lupus erythematosus, CNS disorders such as Alzheimer's disease, arthritis, sepsis, inflammatory bowel disease, cachexia, angina pectoris, post-surgical corneal inflammation, blepharitis, meibomian gland dysfunction, glaucoma, branch vein occlusion, Best's vitelliform macular degeneration, retinitis pigmentosa, proliferative vitreoretinopathy (PVR), and any other degenerative disease of either the photoreceptors or the RPE. The present invention further concerns the use of a compound of Formula I or a pharmaceutically acceptable salt thereof, for the manufacture of a medicament for the treatment of dermal inflammation and dermal diseases or conditions including but not limited to dermal wound healing, hypertrophic scars, keloids, burns, rosacea, atopic dermatitis, acne, psoriasis, seborrheic dermatitis, actinic keratoses, basal cell carcinoma, squamous cell carcinoma, melanoma, viral warts, photoaging, photodamage, melasma, post-inflammatory hyperpigmentation, disorders of pigmentation, alopecia, scarring and non-scarring forms.

The actual amount of the compound to be administered in any given case will be determined by a physician taking into account the relevant circumstances, such as the severity of the condition, the age and weight of the patient, the patient's general physical condition, the cause of the condition, and the route of administration.

The patient will be administered the compound orally in any acceptable form, such as a tablet, liquid, capsule, powder and the like, or other routes may be desirable or necessary, particularly if the patient suffers from nausea. Such other routes may include, without exception, transdermal, parenteral, subcutaneous, intranasal, via an implant stent, intrathecal, intravitreal, topical to the eye, back to the eye, intramuscular, intravenous, and intrarectal modes of delivery. Additionally, the formulations may be designed to delay release of the active compound over a given period of time, or to carefully control the amount of drug released at a given time during the course of therapy.

In another embodiment of the invention, there are provided pharmaceutical compositions including at least one compound of the invention in a pharmaceutically acceptable carrier thereof. The phrase "pharmaceutically acceptable" means the carrier, diluent or excipient must be compatible with the other ingredients of the formulation and not deleterious to the recipient thereof.

Pharmaceutical compositions of the present invention can be used in the form of a solid, a solution, an emulsion, a dispersion, a patch, a micelle, a liposome, and the like, wherein the resulting composition contains one or more compounds of the present invention, as an active ingredient, in admixture with an organic or inorganic carrier or excipient suitable for enteral or parenteral applications. Invention compounds may be combined, for example, with the usual non-toxic, pharmaceutically acceptable carriers for tablets, pellets, capsules, suppositories, solutions, emulsions, suspensions, and any other form suitable for use. The carriers which can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition, auxiliary, stabilizing, thickening and coloring agents and perfumes may be used. Invention compounds are included in the pharmaceutical composition in an amount sufficient to produce the desired effect upon the process or disease condition.

Pharmaceutical compositions containing invention compounds may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known in the art for the manufacture of pharmaceutical compositions and such compositions may contain one or more agents selected from the group consisting of a sweetening agent such as sucrose, lactose, or saccharin, flavoring agents such as peppermint, oil of wintergreen or cherry, coloring agents and preserving agents in order to provide pharmaceutically elegant and palatable preparations. Tablets containing invention compounds in admixture with non-toxic pharmaceutically acceptable excipients may also be manufactured by known methods. The excipients used may be, for example, (1) inert diluents such as calcium carbonate, lactose, calcium phosphate or sodium phosphate; (2) granulating and disintegrating agents such as corn starch, potato starch or alginic acid; (3) binding agents such as gum tragacanth, corn starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed.

In some cases, formulations for oral use may be in the form of hard gelatin capsules wherein the invention compounds are mixed with an inert solid diluent, for example, calcium carbonate, calcium phosphate or kaolin. They may also be in the form of soft gelatin capsules wherein the invention compounds are mixed with water or an oil medium, for example, peanut oil, liquid paraffin or olive oil.

The pharmaceutical compositions may be in the form of a sterile injectable suspension. This suspension may be formulated according to known methods using suitable dispersing or wetting agents and suspending agents. The sterile injectable preparation may also be a sterile injectable solution or suspension in a non-toxic parenterally-acceptable diluent or solvent, for example, as a solution in 1,3-butanediol. Sterile, fixed oils are conventionally employed as a solvent or suspending medium. For this purpose any bland fixed oil may be employed including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate or the like. Buffers, preservatives, antioxidants, and the like can be incorporated as required.

Pharmaceutical compositions containing invention compounds may be in a form suitable for topical use, for example, as oily suspensions, as solutions or suspensions in aqueous liquids or nonaqueous liquids, or as oil-in-water or water-in-oil liquid emulsions. Pharmaceutical compositions may be prepared by combining a therapeutically effective amount of at least one compound according to the present invention, or a pharmaceutically acceptable salt thereof, as an active ingredient with conventional ophthalmically acceptable pharmaceutical excipients and by preparation of unit dosage suitable for topical ocular use. The therapeutically efficient amount typically is between about 0.0001 and about 5% (w/v), preferably about 0.001 to about 2.0% (w/v) in liquid formulations.

For ophthalmic application, preferably solutions are prepared using a physiological saline solution as a major vehicle. The pH of such ophthalmic solutions should preferably be maintained between 4.5 and 8.0 with an appropriate buffer system, a neutral pH being preferred but not essential. The formulations may also contain conventional pharmaceutically acceptable preservatives, stabilizers and surfactants. Preferred preservatives that may be used in the pharmaceutical compositions of the present invention include, but are not limited to, benzalkonium chloride, chlorobutanol, thimerosal, phenylmercuric acetate and phenylmercuric nitrate. A preferred surfactant is, for example, Tween 80. Likewise, various preferred vehicles may be used in the ophthalmic preparations of the present invention. These vehicles include, but are not limited to, polyvinyl alcohol, povidone, hydroxypropyl methyl cellulose, poloxamers, carboxymethyl cellulose, hydroxyethyl cellulose cyclodextrin and purified water.

Tonicity adjustors may be added as needed or convenient. They include, but are not limited to, salts, particularly sodium chloride, potassium chloride, mannitol and glycerin, or any other suitable ophthalmically acceptable tonicity adjustor.

Various buffers and means for adjusting pH may be used so long as the resulting preparation is ophthalmically acceptable. Accordingly, buffers include acetate buffers, citrate buffers, phosphate buffers and borate buffers. Acids or bases may be used to adjust the pH of these formulations as needed.

In a similar manner an ophthalmically acceptable antioxidant for use in the present invention includes, but is not limited to, sodium metabisulfite, sodium thiosulfate, acetylcysteine, butylated hydroxyanisole and butylated hydroxytoluene.

Other excipient components which may be included in the ophthalmic preparations are chelating agents. The preferred chelating agent is edetate disodium, although other chelating agents may also be used in place of or in conjunction with it.

The ingredients are usually used in the following amounts:

| Ingredient | Amount (% w/v) |
| --- | --- |
| active ingredient | about 0.001-5 |
| preservative | 0-0.10 |
| vehicle | 0-40 |
| tonicity adjustor | 0-10 |
| buffer | 0.01-10 |
| pH adjustor | q.s. pH 4.5-7.8 |
| antioxidant | as needed |
| surfactant | as needed |
| purified water | to make 100%. |

The actual dose of the active compounds of the present invention depends on the specific compound, and on the condition to be treated; the selection of the appropriate dose is well within the knowledge of the skilled artisan.

The ophthalmic formulations of the present invention are conveniently packaged in forms suitable for metered application, such as in containers equipped with a dropper, to facilitate application to the eye. Containers suitable for dropwise application are usually made of suitable inert, non-toxic plastic material, and generally contain between about 0.5 and about 15 ml solution. One package may contain one or more unit doses. Especially preservative-free solutions are often formulated in non-resealable containers containing up to about ten, preferably up to about five unit doses, where a typical unit dose is from one to about 8 drops, preferably one to about 3 drops. The volume of one drop usually is about 20-35 microliters.

The compounds of the invention may also be administered in the form of suppositories for rectal administration of the drug. These compositions may be prepared by mixing the invention compounds with a suitable non-irritating excipient, such as cocoa butter, synthetic glyceride esters of polyethylene glycols, which are solid at ordinary temperatures, but liquefy and/or dissolve in the rectal cavity to release the drug.

Since individual subjects may present a wide variation in severity of symptoms and each drug has its unique therapeutic characteristics, the precise mode of administration and dosage employed for each subject is left to the discretion of the practitioner.

The compounds and pharmaceutical compositions described herein are useful as medicaments in mammals, including humans, for treatment of diseases and/or alleviations of conditions which are responsive to treatment by agonists or functional antagonists of the N-formyl peptide 2 receptor. Thus, in further embodiments of the invention, there are provided methods for treating a disorder associated with modulation of the N-formyl peptide 2 receptor. Such methods can be performed, for example, by administering to a subject in need thereof a pharmaceutical composition containing a therapeutically effective amount of at least one invention compound. As used herein, the term "therapeutically effective amount" means the amount of the pharmaceutical composition that will elicit the biological or medical response of a subject in need thereof that is being sought by the researcher, veterinarian, medical doctor or other clinician. In some embodiments, the subject in need thereof is a mammal. In some embodiments, the mammal is human.

The present invention concerns also processes for preparing the compounds of Formula I. The compounds of Formula I according to the invention can be prepared analogously to conventional methods as understood by the person skilled in the art of synthetic organic chemistry.

Synthetic Scheme 1 set forth below illustrates how the compounds according to the invention can be made. Those skilled in the art will be able to routinely modify and/or adapt the following scheme to synthesize any compounds of the invention covered by Formula I or their synthetic precursors.

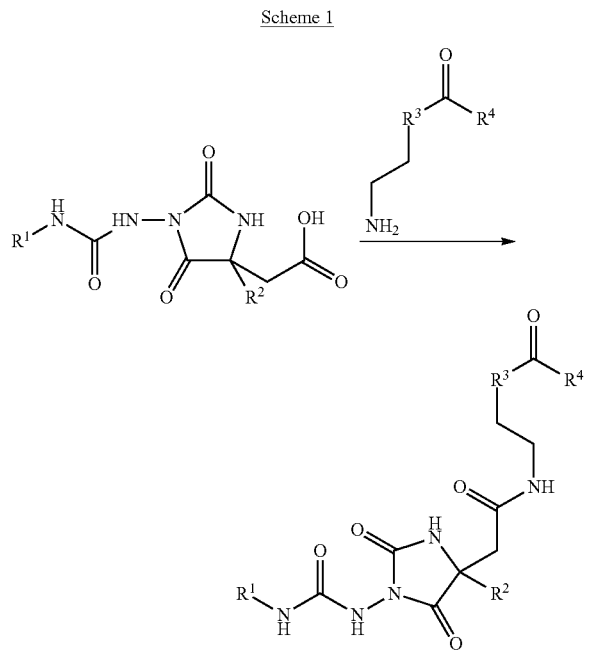

Scheme 1

Compounds within the scope of the invention may be prepared as depicted in Scheme 1. In general, a 2-(4-alkyl-1-(3-phenylureido)-2,5-dioxoimidazolidin-4-yl)acetic acid, which can be prepared according to methods essentially as described in U.S. Pat. No. 8,492,556, is reacted with an appropriately substituted amine to provide compounds of Formula I. Details of certain specific chemical transformations are provided in the examples. Those skilled in the art will be able to routinely modify and/or adapt the following scheme to synthesize any compounds of the invention covered by Formula I.

DRAWINGS

FIG. 1 shows the structure of Formula I.

DETAILED DESCRIPTION OF THE INVENTION

It is to be understood that both the foregoing general description and the following detailed description are exemplary and explanatory only and are not restrictive of the invention claimed. As used herein, the use of the singular includes the plural unless specifically stated otherwise.

It will be readily apparent to those skilled in the art that some of the compounds of the invention may contain one or more asymmetric centers, such that the compounds may exist in enantiomeric as well as in diastereomeric forms.

Unless it is specifically noted otherwise, the scope of the present invention includes all enantiomers, diastereomers and racemic mixtures. As will be evident to those skilled in the art, individual diastereoisomeric forms can be obtained by separation of mixtures thereof in conventional manner; chromatographic separation may be employed.

Some of the compounds of the invention may form salts with pharmaceutically acceptable acids or bases, and such pharmaceutically acceptable salts of the compounds described herein are also within the scope of the invention.

The present invention includes all pharmaceutically acceptable isotopically enriched compounds. Any compound of the invention may contain one or more isotopic atoms enriched or different than the natural ratio such as deuterium $^2H$ (or D) in place of hydrogen $^1H$ (or H) or use of $^{13}C$ enriched material in place of $^{12}C$ and the like. Similar substitutions can be employed for N, O and S. The use of isotopes may assist in analytical as well as therapeutic aspects of the invention. For example, use of deuterium may increase the in vivo half-life by altering the metabolism (rate) of the compounds of the invention. These compounds can be prepared in accord with the preparations described by use of isotopically enriched reagents.

Non-limiting embodiments of the invention are as follows.

In embodiment (1), there is provided a compound represented by Formula I:

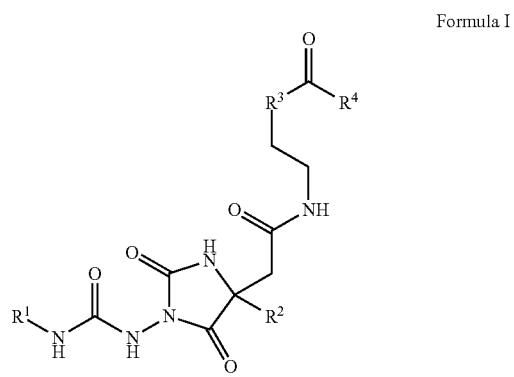

Formula I wherein:
$R^1$ is substituted or unsubstituted $C_{1-8}$alkyl, substituted or unsubstituted $C_{3-8}$cycloalkyl, substituted or unsubstituted $C_6$-$C_{10}$aryl, or substituted or unsubstituted heterocycle;
$R^2$ is hydrogen, or substituted or unsubstituted $C_{1-8}$alkyl;
$R^3$ is O or $NR^5$;
$R^4$ is $C_{1-4}$alkyl; and
$R^5$ is hydrogen, substituted or unsubstituted $C_{1-8}$alkyl, —C(O)$C_{1-8}$alkyl, substituted or unsubstituted $C_6$-$C_{10}$aryl, or substituted or unsubstituted heterocycle;
or an enantiomer, diastereomer or tautomer thereof;
or a pharmaceutically acceptable salt of the foregoing;
wherein:
each substituted $C_{1-8}$alkyl is independently substituted with one or more halogen, hydroxyl, —O$C_{1-8}$ alkyl, $C_{3-8}$cycloalkyl, amino, heterocyclyl, $C_6$-$C_{10}$aryl, carboxylic acid, phosphonic acid, sulphonic acid, phosphoric acid, nitro, amide, sulfonamide, ester or ketone;
each substituted $C_{3-8}$cycloalkyl is independently substituted with one or more halogen, sulfonyl $C_{1-8}$alkyl, sulfoxide $C_{1-8}$alkyl, sulfonamide, nitro, —O$C_{1-8}$ alkyl, —S$C_{1-8}$ alkyl, —$C_{1-8}$ alkyl, ketone, alkylamino, amino, $C_6$-$C_{10}$aryl, $C_{3-8}$ cycloalkyl or hydroxyl;

each substituted $C_6$-$C_{10}$aryl is independently substituted with one or more halogen, sulfonyl sulfoxide $C_{1-8}$alkyl, sulfonamide, carboxylic acid, $C_{1-8}$ alkyl carboxylate (ester), amide, nitro, —$OC_{1-8}$ alkyl, —$SC_{1-8}$ alkyl, —$C_{1-8}$ alkyl, ketone, $C_{1-8}$alkylamino, amino, $C_{3-8}$cycloalkyl or hydroxyl; and each substituted heterocycle is independently substituted with one or more halogen, sulfonyl, sulfoxide, nitro, —$OC_{1-8}$alkyl, —$SC_{1-8}$ alkyl, —$C_{1-8}$alkyl, ketone, $C_{1-8}$alkylamino, amino, $C_6$-$C_{10}$aryl, $C_{3-8}$cycloalkyl or hydroxyl.

In embodiment (2), there is provided a compound of embodiment (1), wherein $R^1$ is substituted or unsubstituted $C_6$aryl.

In embodiment (3), there is provided a compound of embodiment (1) or (2), wherein $R^1$ is $C_6$aryl substituted with at least one halogen.

In embodiment (4), there is provided a compound of any one of embodiments (1), (2) or (3), wherein $R^1$ is substituted phenyl.

In embodiment (5), there is provided a compound of any one of embodiments (1) through (4), wherein $R^1$ is phenyl substituted with at least one halogen.

In embodiment (6), there is provided a compound of any one of embodiments (1) through (5), wherein $R^1$ is 4-bromophenyl or 4-bromo-2-fluorophenyl.

In embodiment (7), there is provided a compound of any one of embodiments (1) through (6), wherein $R^4$ is methyl.

In embodiment (8), there is provided a compound of any one of embodiments (1) through (7), wherein $R^2$ is hydrogen or unsubstituted In embodiment (9), there is provided a compound of any one of embodiments (1) through (8), wherein $R^2$ is methyl, ethyl, n-propyl or isopropyl.

In embodiment (10), there is provided a compound of any one of embodiments (1) through (9), wherein $R^3$ is O.

In embodiment (11), there is provided a compound of any one of embodiments (1) through (9), wherein $R^3$ is $NR^5$.

In embodiment (12), there is provided a compound of any one of embodiments (1) through (9) or (11), wherein $R^3$ is $NR^5$ and $R^5$ is hydrogen.

In embodiment (13), there is provided a compound of any one of embodiments (1) through (12), wherein each $C_{1-8}$ alkyl is independently optionally replaced with $C_{1-4}$alkyl.

In embodiment (14), there is provided a compound of embodiment (13), wherein each $C_{1-4}$alkyl is independently selected from methyl, ethyl, n-propyl, isopropyl, butyl, tert-butyl, isobutyl and sec-butyl.

In embodiment (15), there is provided a compound selected from:
N-[2-(acetylamino)ethyl]-2-[1-{[(4-bromophenyl)carbamoyl]amino}-2,5-dioxo-4-(propan-2-yl)imidazolidin-4-yl]acetamide;
2-({1-{[(4-bromo-2-fluorophenyl)carbamoyl]amino}-2,5-dioxo-4-(propan-2-yl)imidazolidin-4-yl]acetyl}amino)ethyl acetate; and
2-({1-{[(4-bromophenyl)carbamoyl]amino}-2,5-dioxo-4-(propan-2-yl)imidazolidin-4-yl]acetyl}amino)ethyl acetate.

In embodiment (16), there is provided a pharmaceutical composition comprising as active ingredient a therapeutically effective amount of a compound according to any one of embodiments (1) through (15), and a pharmaceutically acceptable carrier.

In embodiment (17), there is provided a compound or pharmaceutical composition according to any one of embodiments (1) through (16) for use in treating an inflammatory disease or condition.

In embodiment (18), there is provided a compound or pharmaceutical composition according to any one of embodiments (1) through (16) for use in treating an inflammatory disease or condition, wherein the disease or condition is an ocular inflammatory disease or condition or a dermal inflammatory disease or condition.

In embodiment (19), there is provided method of treating an inflammatory disease or condition in a subject in need thereof, the method comprising administering a therapeutically effective amount of a compound or pharmaceutical composition according to any one of embodiments (1) through (16) to the subject, thereby treating the condition.

In embodiment (20), there is provided the method of embodiment (19), wherein the disease or condition is an ocular inflammatory disease or condition or a dermal inflammatory disease or condition.

The following examples are for illustrative purposes only and are not intended, nor should they be construed, as limiting the invention in any manner. Those skilled in the art will appreciate that variations and modifications of the following examples can be made without exceeding the spirit or scope of the invention.

Compound names were generated with ACD/Labs version 12.5. Some of the intermediate and reagent names used in the examples were generated with software such as Chem Bio Draw Ultra version 12.0 or Auto Nom 2000 from MDL ISIS Draw 2.5 SP1.

In general, characterization of the compounds was performed according to the following methods. NMR spectra were recorded on a 300 or 600 MHz Varian NMR spectrometer and acquired at room temperature. Chemical shifts are given in ppm referenced either to internal TMS or to the solvent signal. Optical rotations were recorded on Perkin Elmer Polarimeter 341, 589 nm at 20° C., Na/Hal lamp.

All the reagents, solvents, catalysts for which the synthesis is not described were purchased from chemical vendors such as Sigma Aldrich, Fluka, Bio-Blocks, Combi-blocks, TCI, VWR, Lancaster, Oakwood, Trans World Chemical, Alfa, Fisher, Maybridge, Frontier, Matrix, Ukrorgsynth, Toronto, Ryan Scientific, SiliCycle, Anaspec, Syn Chem, Chem-Impex, MIC-scientific, Ltd; however some known intermediates, were prepared according to published procedures.

Usually the compounds of the invention were purified by column chromatography (Auto-column) on Teledyne-ISCO CombiFlash with a silica column, unless noted otherwise.

The following abbreviations are used in the examples:
THF tetrahydrofuran
$CD_3OD$ deuterated methanol
RT room temperature
DMAP 4-dimethylaminopyridine
EDC.HCl [3-(dimethylamino)propyl]ethylcarbodiimide hydrochloride
HOBt 1-hydroxybenzotriazole
$CH_2Cl_2$ dichloromethane
$Ac_2O$ acetic anhydride

EXAMPLE A 2-(1-(3-(4-bromophenyl)ureido)-4-isopropyl-2,5-dioxoimidazolidin-4-yl)acetic acid and 2-(1-(3-(4-bromo-2-fluorophenyl)ureido)-4-isopropyl-2,5-dioxoimidazolidin-4-yl)-N-(2-hydroxyethyl)acetamide were prepared according to methods essentially as described in U.S. Pat. No. 8,492,556.

Example 1

Compound 1

N-[2-(Acetylamino)ethyl]-2-[1-{[(4-Bromophenyl)carbamoyl]amino}-2,5-dioxo-4-(propan-2-yl)imidazolidin-4-yl]acetamide

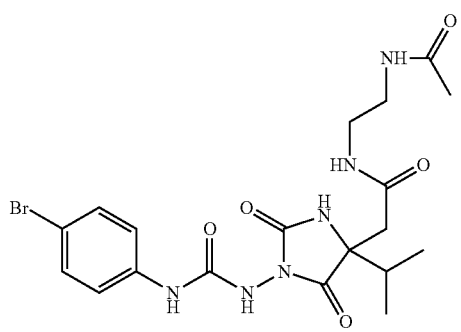 [SMILES: CC(=O)NCCNC(=O)CC1(C(C)C)NC(=O)N(NC(=O)Nc2ccc(Br)cc2)C1=O]

A solution of 2-(1-(3-(4-bromophenyl)ureido)-4-isopropyl-2,5-dioxo imidazolidin-4-yl)acetic acid [CAS #1434719-32-0] (40 mg, 0.1 mmol), N-(2-aminoethyl)acetamide (30 mg, 0.3 mmol), HOBt [CAS #2592-95-2] (40 mg, 0.3 mmol), EDC.HCl [CAS #25952-53-8] (60 mg, 0.3 mmol), 4-methyl morpholine (50 mg, 0.5 mmol) and $CH_2Cl_2$ (10 mL) was stirred at RT for 3 days. The solvent was removed under reduced pressure and the crude product was purified by silica gel chromatography. Compound 1 was isolated as a white solid.

$^1$HNMR ($CD_3OD$) δ: 0.94 (d, J=6.7 Hz, 3H), 1.02 (d, J=6.7 Hz, 3H), 1.91 (s, 3H), 1.98-2.06 (m, 1H), 2.72-3.02 (m, 2H), 3.40-3.70 (m, 4H), 7.40 (d, J=8.5 Hz, 2H), 7.55 (d, J=8.5 Hz, 2H).

Example 2

Compound 2

2-({[1-{[(4-Bromo-2-Fluorophenyl)carbamoyl]amino}-2,5-dioxo-4-(propan-2-yl)imidazolidin-4-yl]acetyl}amino)ethyl acetate

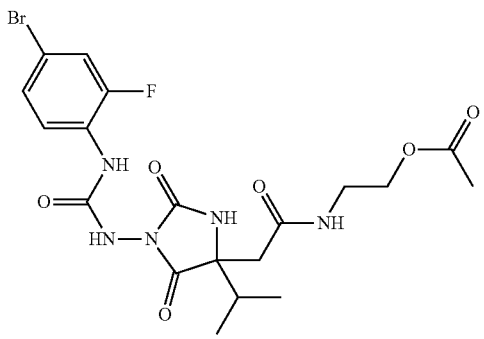 [SMILES: CC(=O)OCCNC(=O)CC1(C(C)C)NC(=O)N(NC(=O)Nc2ccc(Br)cc2F)C1=O]

A solution of 2-(1-(3-(4-Bromo-2-Fluorophenyl)ureido)-4-isopropyl-2,5-dioxoimidazolidin-4-yl)-N-(2-hydroxyethyl)acetamide [CAS #1434720-56-5] (70 mg, 0.15 mmol), $Ac_2O$ (17 mg, 0.16 mmol), and DMAP (20 mg) in THF (5 mL) was stirred for 90 min at RT. The solvent was removed under reduced pressure and the crude product was purified by silica gel chromatography. Compound 2 was isolated as a white solid.

$^1$HNMR ($CD_3OD$) δ: 0.87-1.08 (m, 6H), 1.90-2.12 (m, 4H), 2.85 (d, J=8.8 Hz, 2H), 3.37 (br s, 2H), 4.04 (t, J=5.3 Hz, 2H), 7.29 (d, J=8.2 Hz, 1H), 7.35 (d, J=10.3 Hz, 1H), 7.67 (br s, 1H).

Example 3

Compound 3

2-({[1-{[(4-Bromophenyl)carbamoyl]amino}-2,5-Dioxo-4-(propan-2-yl)imidazolidin-4-yl]acetyl}amino)ethyl acetate

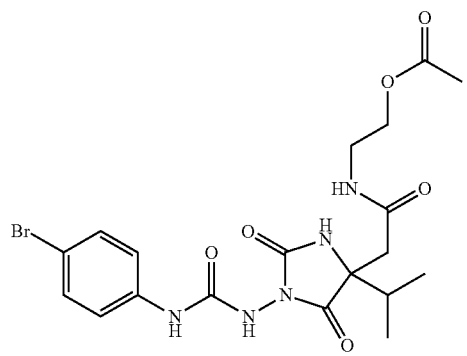 [SMILES: CC(=O)OCCNC(=O)CC1(C(C)C)NC(=O)N(NC(=O)Nc2ccc(Br)cc2)C1=O]

A solution of 2-(1-(3-(4-bromophenyl)ureido)-4-isopropyl-2,5-dioxoimidazolidin-4-yl)acetic acid [CAS #1434719-32-0] (32 mg, 0.08 mmol), N-2-aminoethyl acetate (8 mg, 0.08 mmol), HOBt [CAS #2592-95-2] (32 mg, 0.24 mmol), EDC.HCl (CAS #25952-53-8) (46 mg, 0.24 mmol), 4-methyl morpholine (40 mg, 0.4 mmol) and $CH_2Cl_2$ (5 mL) was stirred at RT for 18 h. The solvent was removed under reduced pressure and the crude product was purified by silica gel chromatography. Compound 3 was isolated as a white solid.

$^1$HNMR ($CD_3OD$) δ: 0.99 (d, J=6.7 Hz, 3H), 1.03 (d, J=6.7 Hz, 3H), 1.93 (s, 3H), 1.98-2.10 (m, 1H), 2.96-3.10 (m, 2H), 3.40-3.70 (m, 2H), 4.19 (br s, 2H), 7.42 (br s, 4H).

Biological Data

Biological activity of compounds according to Formula I is set forth in Table 1 below. CHO-Gα16 cells stably expressing FPR2 were cultured in F12 media (10% FBS, 1% PSA, 400 µg/ml geneticin and 50 µg/ml hygromycin). In general, the day before the experiment, 18,000 cells/well were plated in a 384-well clear bottom poly-D-lysine coated plate. The following day the screening compound-induced calcium activity was assayed on a FLIPR$^{Tetra}$. The drug plates were prepared in 384-well microplates using EP3 and MultiPROBE robotic liquid handling systems. Compounds were tested at concentrations ranging from 0.61 to 10,000 nM. Results are expressed as $EC_{50}$ (nM) and % efficacy values.

TABLE 1

| Compound | IUPAC name | FPR2 Gα16-CHO EC50 nM (%eff) |
|---|---|---|
| 1 | N-[2-(Acetylamino)ethyl]-2-[1-{[(4-bromophenyl)carbamoyl] amino}-2,5-dioxo-4-(propan-2-yl)imidazolidin-4-yl]acetamide | 6 (0.94) |
| 2 | 2-({[1-{[(4-Bromo-2-fluorophenyl)carbamoyl]amino}-2,5-dioxo-4-(propan-2-yl)imidazolidin-4-yl]acetyl}amino)ethyl acetate | 4 (0.94) |
| 3 | 2-({[1-{[(4-Bromophenyl)carbamoyl]amino}-2,5-dioxo-4-(propan-2-yl)imidazolidin-4-yl]acetyl}amino)ethyl acetate | 10 (0.97) |

What we claim is:

1. A compound represented by Formula I:

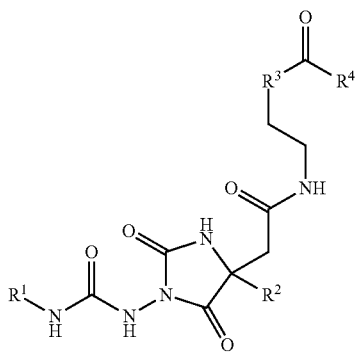

Formula I wherein:

$R^1$ is optionally substituted $C_{1-8}$alkyl, optionally substituted $C_{3-8}$cycloalkyl, optionally substituted $C_6$-$C_{10}$aryl, or optionally substituted heterocycle;
$R^2$ is hydrogen or optionally substituted $C_{1-8}$alkyl;
$R^3$ is O or $NR^5$;
$R^4$ is $C_{1-4}$alkyl; and
$R^5$ is hydrogen, optionally substituted $C_{1-8}$alkyl, —C(O) $C_{1-8}$alkyl, optionally substituted $C_6$-$C_{10}$aryl, or optionally substituted heterocycle;

or an enantiomer, diastereomer or tautomer thereof;
or a pharmaceutically acceptable salt of the foregoing.

2. A compound according to claim 1, wherein $R^3$ is O.

3. A compound according to claim 1, wherein $R^3$ is $NR^5$, and $R^5$ is hydrogen.

4. A compound according to claim 1, wherein $R^1$ is substituted $C_6$aryl.

5. A compound according to claim 1, wherein $R^1$ is substituted phenyl.

6. A compound according to claim 5, wherein $R^1$ is phenyl substituted with one or more halogens.

7. A compound according to claim 1, wherein $R^4$ is methyl.

8. A compound according to claim 1, wherein $R^2$ is methyl, ethyl, n-propyl or isopropyl.

9. A compound according to claim 1, selected from:
N-[2-(acetylamino)ethyl]-2-[1-{[(4-bromophenyl)carbamoyl]amino}-2,5-dioxo-4-(propan-2-yl)imidazolidin-4-yl]acetamide;
2-({[1-{[(4-bromo-2-fluorophenyl)carbamoyl]amino}-2,5-dioxo-4-(propan-2-yl)imidazolidin-4-yl]acetyl}amino)ethyl acetate; and
2-({[1-{[(4-bromophenyl)carbamoyl] amino}-2,5-dioxo-4-(propan-2-yl)imidazolidin-4-yl]acetyl}amino)ethyl acetate.

10. A pharmaceutical composition comprising as active ingredient a therapeutically effective amount of a compound according to claim 1 and a pharmaceutically acceptable carrier.

11. A pharmaceutical composition according to claim 10, wherein the compound is selected from:
N-[2-(acetylamino)ethyl]-2-[1-{[(4-bromophenyl)carbamoyl]amino}-2,5-dioxo-4-(propan-2-yl)imidazolidin-4-yl]acetamide;
2-({[1-{[(4-bromo-2-fluorophenyl)carbamoyl]amino}-2,5-dioxo-4-(propan-2-yl)imidazolidin-4-yl]acetyl}amino)ethyl acetate; and
2-({[1-{[(4-bromophenyl)carbamoyl] amino}-2,5-dioxo-4-(propan-2-yl)imidazolidin-4-yl]acetyl}amino)ethyl acetate.

* * * * *